(12) United States Patent
Solsberg et al.

(10) Patent No.: US 7,896,879 B2
(45) Date of Patent: Mar. 1, 2011

(54) SPINAL LIGAMENT MODIFICATION

(75) Inventors: Murray David Solsberg, Englewood, CO (US); Donald Schomer, Englewood, CO (US); Bryce Way, San Jose, CA (US)

(73) Assignee: Vertos Medical, Inc., Aliso Viejo, CA (US)

( * ) Notice: Subject to any disclaimer, the term of this patent is extended or adjusted under 35 U.S.C. 154(b) by 1586 days.

(21) Appl. No.: 11/193,581

(22) Filed: Jul. 29, 2005

(65) Prior Publication Data

US 2006/0036272 A1    Feb. 16, 2006

Related U.S. Application Data

(60) Provisional application No. 60/592,099, filed on Jul. 29, 2004.

(51) Int. Cl.
*A61M 31/00*    (2006.01)
(52) U.S. Cl. .......................................................... 606/79
(58) Field of Classification Search .................... 606/79, 606/93; 604/48; 623/17.11–17.16
See application file for complete search history.

(56) References Cited

U.S. PATENT DOCUMENTS

| | | |
|---|---|---|
| 1,493,240 A | 5/1924 | Bohn |
| 3,628,524 A | 12/1971 | Jamshidi |
| 3,732,858 A | 5/1973 | Banko |
| 3,893,445 A | 7/1975 | Hofsess |
| 3,929,123 A | 12/1975 | Jamshidi |
| 3,945,372 A | 3/1976 | Milan et al. |
| 4,103,690 A | 8/1978 | Harris |
| 4,174,715 A | 11/1979 | Hasson |
| 4,200,111 A | 4/1980 | Harris |
| 4,201,213 A | 5/1980 | Townsend |
| 4,283,129 A | 8/1981 | Bennick, Jr. |
| 4,535,773 A | 8/1985 | Yoon |
| 4,603,694 A | 8/1986 | Wheeler |
| 4,682,606 A | 7/1987 | DeCaprio |

(Continued)

FOREIGN PATENT DOCUMENTS

GB    2177307    1/1987

(Continued)

OTHER PUBLICATIONS

International Search Report and Written Opinion for Appl. No. PCT/US2006/030299 dated Aug. 2007 (8 p.).

(Continued)

*Primary Examiner* — Thomas C Barrett
*Assistant Examiner* — Christopher Beccia
(74) *Attorney, Agent, or Firm* — Finnegan, Henderson, Farabow, Garrett & Dunner, LLP

(57) ABSTRACT

A method for treating stenosis in a spine comprises percutaneously accessing the epidural space in a stenotic region of interest, compressing the thecal sac in the region of interest to form a safety zone, inserting a tissue removal tool into tissue in the working zone, using the tool to percutaneously reduce the stenosis; and utilizing imaging to visualize the position of the tool during at least a part of the reduction step. A tissue excision system for performing percutaneous surgery, comprises a cannula comprising a tissue-penetrating member having a distal end defining an aperture on one side thereof, an occluding member slidably received on or in the cannula and closing the aperture when the occluding member is adjacent the cannula distal end, means for engaging adjacent tissue via the aperture, and cutting means for resecting a section of the engaged tissue.

20 Claims, 8 Drawing Sheets

U.S. PATENT DOCUMENTS

| | | |
|---|---|---|
| 4,708,147 A | 11/1987 | Haaga |
| 4,733,663 A | 3/1988 | Farley |
| 4,777,948 A | 10/1988 | Wright |
| 4,801,293 A | 1/1989 | Jackson |
| 4,811,734 A | 3/1989 | McGurk-Burleson et al. |
| 4,834,729 A | 5/1989 | Sjostrom |
| 4,844,064 A | 7/1989 | Thimsen et al. |
| 4,850,354 A | 7/1989 | McGurk-Burleson et al. |
| 4,867,157 A | 9/1989 | McGurk-Burleson et al. |
| 4,931,059 A | 6/1990 | Markham |
| 4,991,600 A | 2/1991 | Taylor |
| 4,994,072 A | 2/1991 | Bhate |
| 5,026,375 A | 6/1991 | Linovitz et al. |
| 5,026,386 A | 6/1991 | Michelson |
| 5,040,542 A | 8/1991 | Gray |
| 5,108,403 A | 4/1992 | Stern |
| 5,127,916 A | 7/1992 | Spencer et al. |
| 5,172,702 A | 12/1992 | Leigh et al. |
| 5,180,393 A | 1/1993 | Commarmond |
| 5,190,759 A | 3/1993 | Lindblad et al. |
| 5,215,105 A | 6/1993 | Kizelshteyn et al. |
| 5,226,910 A | 7/1993 | Kajiyama et al. |
| 5,269,785 A | 12/1993 | Bonutti |
| 5,281,230 A | 1/1994 | Heidmueller |
| 5,290,303 A | 3/1994 | Pingleton et al. |
| 5,300,045 A | 4/1994 | Plassche, Jr. |
| 5,320,110 A | 6/1994 | Wang |
| 5,354,266 A | 10/1994 | Snoke |
| 5,366,477 A | 11/1994 | Lemarie et al. |
| 5,373,854 A | 12/1994 | Kolozsi |
| 5,385,570 A | 1/1995 | Chin et al. |
| 5,429,136 A * | 7/1995 | Milo et al. ............... 600/439 |
| 5,429,138 A | 7/1995 | Jamshidi |
| 5,439,464 A | 8/1995 | Shapiro |
| 5,451,227 A | 9/1995 | Michaelson |
| 5,458,112 A | 10/1995 | Weaver |
| 5,462,062 A | 10/1995 | Rubinstein |
| 5,496,269 A | 3/1996 | Snoke |
| 5,514,379 A | 5/1996 | Weissleder et al. |
| 5,522,825 A | 6/1996 | Kropf et al. |
| 5,531,749 A | 7/1996 | Michelson |
| 5,538,008 A | 7/1996 | Crowe |
| 5,540,693 A | 7/1996 | Fisher |
| 5,562,102 A | 10/1996 | Taylor |
| 5,569,258 A | 10/1996 | Gambale |
| 5,569,284 A | 10/1996 | Young et al. |
| 5,578,030 A | 11/1996 | Levin |
| 5,582,618 A | 12/1996 | Chin et al. |
| 5,595,186 A | 1/1997 | Rubinstein et al. |
| 5,613,972 A | 3/1997 | Lee et al. |
| 5,638,827 A | 6/1997 | Palmer et al. |
| 5,645,075 A | 7/1997 | Palmer et al. |
| 5,649,547 A | 7/1997 | Ritchart et al. |
| 5,681,337 A | 10/1997 | Bray, Jr. |
| 5,705,485 A * | 1/1998 | Cini et al. ............... 514/12 |
| 5,709,697 A | 1/1998 | Ratcliff et al. |
| 5,718,237 A * | 2/1998 | Haaga ............... 600/564 |
| 5,730,754 A | 3/1998 | Obenchain |
| 5,735,865 A | 4/1998 | Schaumann et al. |
| 5,759,185 A | 6/1998 | Grinberg et al. |
| 5,772,597 A | 6/1998 | Goldberger et al. |
| 5,775,333 A | 7/1998 | Burbank et al. |
| 5,776,075 A | 7/1998 | Palmer |
| 5,782,849 A | 7/1998 | Miller |
| 5,792,044 A | 8/1998 | Foley et al. |
| 5,797,936 A | 8/1998 | Kleihues |
| 5,797,939 A | 8/1998 | Yoon |
| 5,797,958 A | 8/1998 | Yoon |
| 5,823,970 A | 10/1998 | Terwilliger |
| 5,827,289 A * | 10/1998 | Reiley et al. ............... 606/86 R |
| 5,827,305 A | 10/1998 | Gordon |
| 5,836,948 A | 11/1998 | Zucherman et al. |
| 5,840,338 A | 11/1998 | Roos et al. |
| 5,843,121 A | 12/1998 | Yoon |
| 5,853,366 A | 12/1998 | Dowlatshahi |
| 5,857,996 A | 1/1999 | Snoke |
| 5,860,991 A | 1/1999 | Klein et al. |
| 5,868,745 A | 2/1999 | Alleyne |
| 5,871,453 A | 2/1999 | Banik et al. |
| 5,873,886 A | 2/1999 | Larsen et al. |
| 5,879,353 A | 3/1999 | Terry |
| 5,879,365 A | 3/1999 | Whitfield et al. |
| 5,916,858 A | 6/1999 | Kim et al. |
| 5,925,050 A | 7/1999 | Howard, III |
| 5,925,056 A | 7/1999 | Thomas et al. |
| 5,931,855 A | 8/1999 | Buncke |
| 5,954,739 A * | 9/1999 | Bonutti ............... 606/190 |
| 5,964,782 A | 10/1999 | Lafontaine et al. |
| 5,980,525 A | 11/1999 | Bryant et al. |
| 5,984,939 A | 11/1999 | Yoon |
| 5,985,320 A * | 11/1999 | Edwards et al. ............... 424/450 |
| 6,010,493 A | 1/2000 | Snoke |
| 6,019,765 A | 2/2000 | Thornhill et al. |
| 6,022,362 A | 2/2000 | Lee et al. |
| 6,053,877 A | 4/2000 | Banik et al. |
| 6,083,237 A | 7/2000 | Huitema et al. |
| 6,096,053 A | 8/2000 | Bates |
| 6,110,127 A * | 8/2000 | Suzuki ............... 600/565 |
| 6,142,957 A | 11/2000 | Diamond et al. |
| 6,142,997 A | 11/2000 | Michelson |
| 6,214,010 B1 | 4/2001 | Farley et al. |
| 6,221,006 B1 | 4/2001 | Dubrul et al. |
| 6,241,747 B1 | 6/2001 | Ruff |
| 6,258,093 B1 | 7/2001 | Edwards et al. |
| 6,261,294 B1 | 7/2001 | Stihl et al. |
| 6,261,582 B1 | 7/2001 | Needham et al. |
| 6,264,087 B1 | 7/2001 | Whitman |
| 6,264,617 B1 | 7/2001 | Bales et al. |
| 6,268,405 B1 | 7/2001 | Yao et al. |
| 6,273,862 B1 | 8/2001 | Privitera et al. |
| 6,287,304 B1 | 9/2001 | Eggers et al. |
| 6,296,639 B1 | 10/2001 | Truckai et al. |
| 6,306,156 B1 | 10/2001 | Clark |
| 6,332,886 B1 | 12/2001 | Green et al. |
| 6,358,217 B1 | 3/2002 | Bourassa |
| 6,358,254 B1 | 3/2002 | Anderson |
| 6,371,968 B1 * | 4/2002 | Kogasaka et al. ............... 606/190 |
| 6,375,659 B1 * | 4/2002 | Erbe et al. ............... 606/94 |
| 6,419,684 B1 | 7/2002 | Heisler et al. |
| 6,423,332 B1 | 7/2002 | Huxel et al. |
| 6,425,859 B1 | 7/2002 | Foley et al. |
| 6,428,486 B2 | 8/2002 | Ritchart et al. |
| 6,428,498 B2 | 8/2002 | Uflacker |
| 6,443,910 B1 | 9/2002 | Krueger et al. |
| 6,454,767 B2 | 9/2002 | Alleyne |
| 6,464,682 B1 * | 10/2002 | Snoke ............... 604/510 |
| 6,470,209 B2 | 10/2002 | Snoke |
| 6,478,805 B1 | 11/2002 | Marino et al. |
| 6,488,636 B2 | 12/2002 | Bryan et al. |
| 6,506,190 B1 | 1/2003 | Walshe |
| 6,514,256 B2 | 2/2003 | Zucherman et al. |
| 6,520,907 B1 | 2/2003 | Foley et al. |
| 6,530,933 B1 | 3/2003 | Yeung et al. |
| 6,533,795 B1 | 3/2003 | Tran et al. |
| 6,572,563 B2 | 6/2003 | Ouchi |
| 6,575,919 B1 | 6/2003 | Reiley et al. |
| 6,575,968 B1 | 6/2003 | Eggers et al. |
| 6,579,291 B1 | 6/2003 | Keith et al. |
| 6,599,310 B2 | 7/2003 | Leung et al. |
| 6,602,248 B1 | 8/2003 | Sharps et al. |
| 6,605,294 B2 | 8/2003 | Sawhney |
| 6,620,185 B1 | 9/2003 | Harvie et al. |
| 6,626,916 B1 | 9/2003 | Yeung et al. |
| 6,632,182 B1 | 10/2003 | Treat |
| 6,645,213 B2 | 11/2003 | Sand et al. |
| 6,652,558 B2 | 11/2003 | Patel et al. |
| 6,669,729 B2 | 12/2003 | Chin |
| 6,682,535 B2 | 1/2004 | Hoogland |
| 6,692,445 B2 | 2/2004 | Roberts et al. |
| 6,716,216 B1 * | 4/2004 | Boucher et al. ............... 606/86 R |
| 6,746,093 B2 | 6/2004 | Martinez et al. |
| 6,746,451 B2 | 6/2004 | Middleton et al. |
| 6,772,012 B2 | 8/2004 | Ricart et al. |
| 6,783,534 B2 | 8/2004 | Mehdizadeh |
| 6,818,001 B2 | 11/2004 | Wulfman et al. |
| 6,852,095 B1 | 2/2005 | Ray |
| 6,858,229 B1 | 2/2005 | Hubbell et al. |

| | | |
|---|---|---|
| 6,925,323 B2 | 8/2005 | Snoke |
| 7,008,433 B2 | 3/2006 | Voellmicke et al. |
| 7,025,771 B2 | 4/2006 | Kuslich et al. |
| 7,041,050 B1 * | 5/2006 | Ronald .......... 600/104 |
| 7,066,942 B2 | 6/2006 | Treace |
| 7,070,596 B1 | 7/2006 | Woloszko et al. |
| 7,101,382 B2 * | 9/2006 | George et al. .......... 606/167 |
| 7,104,986 B2 | 9/2006 | Hovda et al. |
| 7,118,576 B2 | 10/2006 | Gitis et al. |
| 7,131,951 B2 | 11/2006 | Angel |
| 7,137,956 B2 | 11/2006 | Nishtalas et al. |
| 7,181,289 B2 | 2/2007 | Pflueger et al. |
| 7,189,206 B2 * | 3/2007 | Quick et al. .......... 600/564 |
| 7,189,240 B1 * | 3/2007 | Dekel .......... 606/85 |
| 7,201,722 B2 | 4/2007 | Krueger |
| 7,226,424 B2 | 6/2007 | Ritchart et al. |
| 7,276,032 B2 | 10/2007 | Hibner |
| 7,309,338 B2 * | 12/2007 | Cragg .......... 606/80 |
| 7,322,978 B2 * | 1/2008 | West, Jr. .......... 606/60 |
| 7,329,402 B2 * | 2/2008 | Unger et al. .......... 424/9.52 |
| 7,445,634 B2 * | 11/2008 | Trieu .......... 623/17.11 |
| 2001/0005778 A1 * | 6/2001 | Ouchi .......... 600/564 |
| 2002/0054915 A1 * | 5/2002 | Goldenheim et al. .......... 424/497 |
| 2003/0009125 A1 | 1/2003 | Nita et al. |
| 2003/0050574 A1 | 3/2003 | Krueger |
| 2003/0077225 A1 | 4/2003 | Laurent et al. |
| 2003/0165555 A1 | 9/2003 | Ding et al. |
| 2003/0220650 A1 | 11/2003 | Major et al. |
| 2004/0024398 A1 * | 2/2004 | Hovda et al. .......... 606/41 |
| 2004/0049217 A1 | 3/2004 | Ross et al. |
| 2004/0059370 A1 | 3/2004 | Greene, Jr. et al. |
| 2004/0138701 A1 | 7/2004 | Haluck |
| 2004/0210231 A1 * | 10/2004 | Boucher et al. .......... 606/93 |
| 2005/0037079 A1 | 2/2005 | Son et al. |
| 2005/0038432 A1 | 2/2005 | Shaolian et al. |
| 2005/0070913 A1 | 3/2005 | Milbocker et al. |
| 2005/0075630 A1 | 4/2005 | Truckai et al. |
| 2005/0080441 A1 | 4/2005 | Dodge et al. |
| 2005/0137602 A1 | 6/2005 | Assell et al. |
| 2005/0163850 A1 | 7/2005 | Wong et al. |
| 2005/0197661 A1 | 9/2005 | Carrison et al. |
| 2005/0209610 A1 | 9/2005 | Carrison |
| 2005/0228403 A1 | 10/2005 | Ho et al. |
| 2005/0261692 A1 | 11/2005 | Carrison et al. |
| 2006/0030785 A1 | 2/2006 | Field et al. |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0089609 A1 | 4/2006 | Bleich et al. |
| 2006/0089633 A1 | 4/2006 | Bleich et al. |
| 2006/0089640 A1 | 4/2006 | Bleich et al. |
| 2006/0094976 A1 | 5/2006 | Bleich |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122535 A1 | 6/2006 | Daum |
| 2006/0135882 A1 | 6/2006 | Bleich |
| 2006/0178682 A1 | 8/2006 | Boehlke |
| 2006/0184175 A1 | 8/2006 | Schomer et al. |
| 2006/0206115 A1 | 9/2006 | Schomer et al. |
| 2006/0224160 A1 | 10/2006 | Trieu et al. |
| 2006/0235334 A1 | 10/2006 | Corvi et al. |
| 2006/0235422 A1 | 10/2006 | Keller |
| 2006/0235451 A1 | 10/2006 | Schomer et al. |
| 2006/0235452 A1 | 10/2006 | Schomer et al. |
| 2006/0264994 A1 | 11/2006 | Schomer et al. |
| 2007/0005084 A1 | 1/2007 | Clague et al. |
| 2007/0027464 A1 | 2/2007 | Way et al. |
| 2007/0055215 A1 | 3/2007 | Tran et al. |
| 2007/0055263 A1 | 3/2007 | Way et al. |
| 2007/0123888 A1 | 5/2007 | Bleich et al. |
| 2007/0123890 A1 | 5/2007 | Way et al. |
| 2007/0162061 A1 | 7/2007 | Way et al. |
| 2007/0198019 A1 | 8/2007 | Schomer et al. |
| 2007/0225703 A1 | 9/2007 | Schmitz et al. |
| 2007/0260253 A1 | 11/2007 | Johnson et al. |
| 2007/0276390 A1 | 11/2007 | Solsberg et al. |
| 2008/0221383 A1 | 9/2008 | Way et al. |
| 2009/0118709 A1 | 5/2009 | Sand et al. |

FOREIGN PATENT DOCUMENTS

| | | |
|---|---|---|
| WO | WO 97/34536 | 9/1997 |
| WO | WO 97/34536 A3 | 11/1997 |
| WO | WO 98/22022 | 5/1998 |
| WO | WO 00/45868 | 8/2000 |
| WO | WO 01/08571 | 2/2001 |
| WO | WO 01/82998 A2 | 11/2001 |
| WO | WO 02/076311 | 10/2002 |
| WO | WO 02/076311 A3 | 2/2004 |
| WO | WO 2006/015302 A1 | 2/2006 |
| WO | WO 2006/044727 A2 | 4/2006 |
| WO | WO 2007/085628 A1 | 8/2007 |
| WO | WO 2007/113808 A1 | 10/2007 |
| WO | WO 2008/042793 A2 | 4/2008 |
| WO | WO 2008/070867 A2 | 6/2008 |
| WO | WO 2008/139260 A2 | 11/2008 |

OTHER PUBLICATIONS

PCT International Search Report and Written Opinion for Appl. No. PCT/US06/04342 dated Sep. 18, 2007 (8 p.).

PCT International Search Report for International Application No. PCT/US05/27216 dated Nov. 29, 2005 (2 p.).

Brunette, J. et al. "Comparative Rheology of Low- and Iso-Osmolarity Contrast Agents at Different Temperatures Catheterization and Cardiovascular Interventions," 71:78-83 (2008).

European Search Report issued in EP 08253596.4, mailed on Mar. 27, 2009.

European Search Report issued in EP 08253854.7, mailed on Apr. 4, 2009.

Great Britain Search Report issued in GB 0821929.7, dated Mar. 2, 2009.

International Search Report and Written Opinion issued in PCT/US2006/30298, mailed on Jan. 11, 2008.

International Search Report and Written Opinion issued in PCT/US2006/30302, mailed on Jul. 3, 2008.

International Search Report and Written Opinion issued in PCT/US2006/43242, mailed on Sep. 18, 2007.

International Search Report and Written Opinion issued in PCT/US2007/68553, mailed on Sep. 11, 2008.

International Search Report issued in PCT/US2008/53681, mailed on Jul. 29, 2008.

Office Action issued in U.S. Appl. No. 10/595,536, mailed on Jan. 21, 2009.

Office Action issued in U.S. Appl. No. 10/595,536, mailed on Jul. 9, 2009.

Office Action issued in U.S. Appl. No. 10/595,536, mailed on May 12, 2008.

Office Action issued in U.S. Appl. No. 11/193,278, mailed on Apr. 22, 2009.

Office Action issued in U.S. Appl. No. 11/193,278, mailed on May 9, 2008.

Office Action issued in U.S. Appl. No. 11/193,278, mailed on Nov. 3, 2008.

Office Action issued in U.S. Appl. No. 11/193,557, mailed on Apr. 28, 2009.

Office Action issued in U.S. Appl. No. 11/193,557, mailed on Nov. 13, 2008.

Office Action issued in U.S. Appl. No. 11/193,559, mailed on Aug. 22, 2008.

Office Action issued in U.S. Appl. No. 11/193,559, mailed on Jun. 24, 2009.

Office Action issued in U.S. Appl. No. 11/382,349, mailed on Feb. 27, 2009.

Office Action issued in U.S. Appl. No. 11/461,036, mailed on May 5, 2009.

Office Action issued in U.S. Appl. No. 11/461,045, mailed on Apr. 1, 2009.

Office Action issued in U.S. Appl. No. 11/555,899, mailed Jul. 8, 2009.

Office Action issued in U.S. Appl. No. 11/556,213, mailed Jul. 23, 2009.
Office Action issued in U.S. Appl. No. 12/188,360, mailed on Mar. 5, 2009.
Written Opinion issued in PCT/US2005/27216, mailed on Jan. 12, 2006.
European Search Report issued in EP 08729616.6, mailed on Feb. 2, 2010.
Office Action issued in U.S. Appl. No. 11/193,557, mailed Jan. 20, 2010.
Office Action issued in U.S. Appl. No. 11/193,559, mailed on Mar. 18, 2010.
Office Action issued in U.S. Appl. No. 11/382,349, mailed on Nov. 24, 2009.
Office Action issued in U.S. Appl. No. 11/556,213, mailed on Apr. 27, 2010.
Office Action issued in U.S. Appl. No. 11/556,213, mailed on Oct. 28, 2009.
Office Action issued in U.S. Appl. No. 10/595,536, mailed on Aug. 26, 2010.
Office Action issued in U.S. Appl. No. 11/380,377, mailed on Jun. 22, 2010.
Office Action issued in U.S. Appl. No. 11/461,036, mailed on Jul. 27, 2010.
Office Action issued in U.S. Appl. No. 11/555,899, mailed on Aug. 4, 2010.
Kashiwagi, K., "Histological Changes of the Lumbar Ligamentum Flavum with Age," (J. Jpn. Orthop. Assoc.) 67:221-229 (1993).
Fong, Sy et al. "Thoracic Myelopathy Secondary to Ligamentum Flavum Ossification," (Ann. Acad. Med. Singapore) 33:340-6 (2004).

* cited by examiner

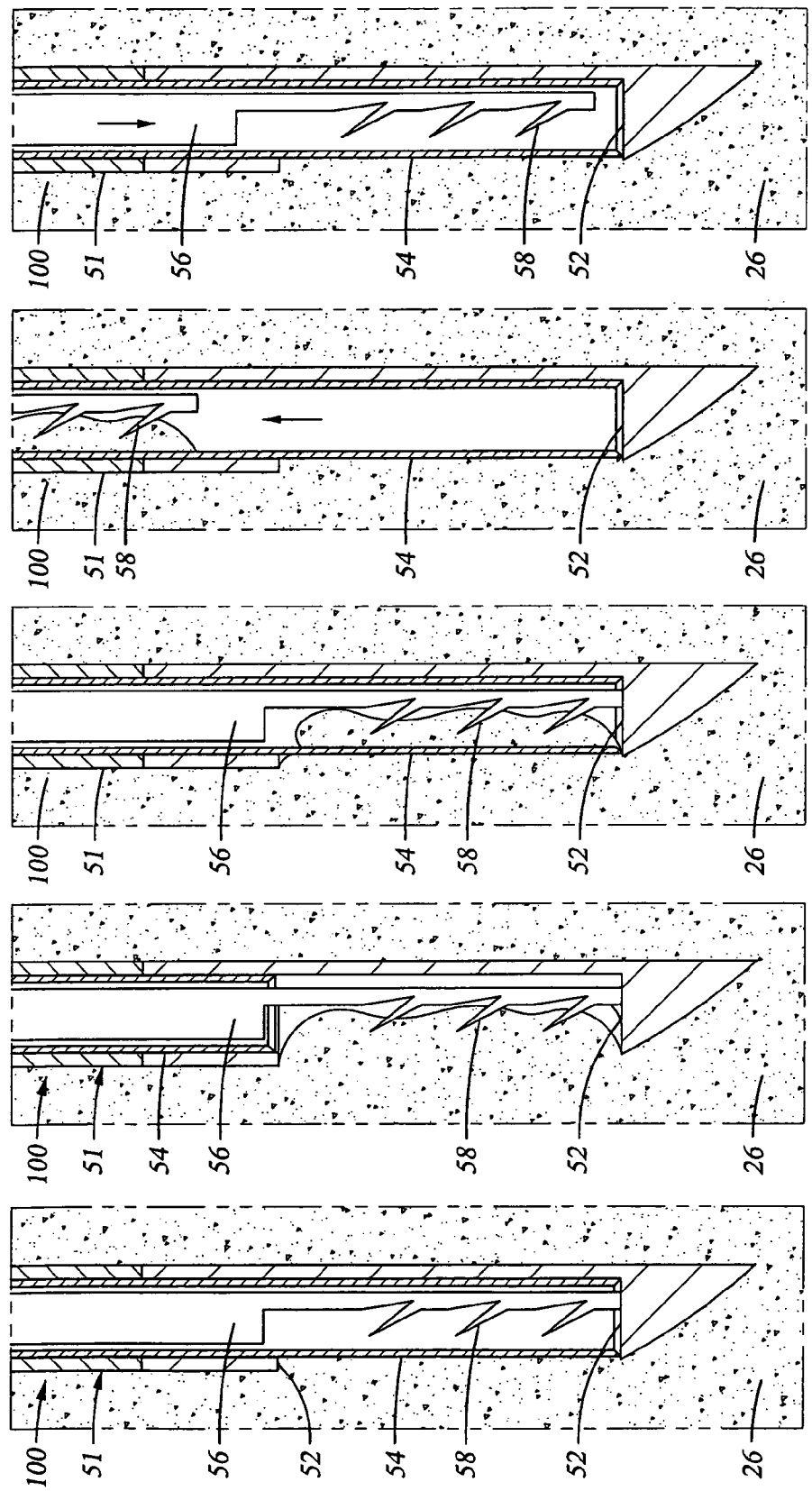

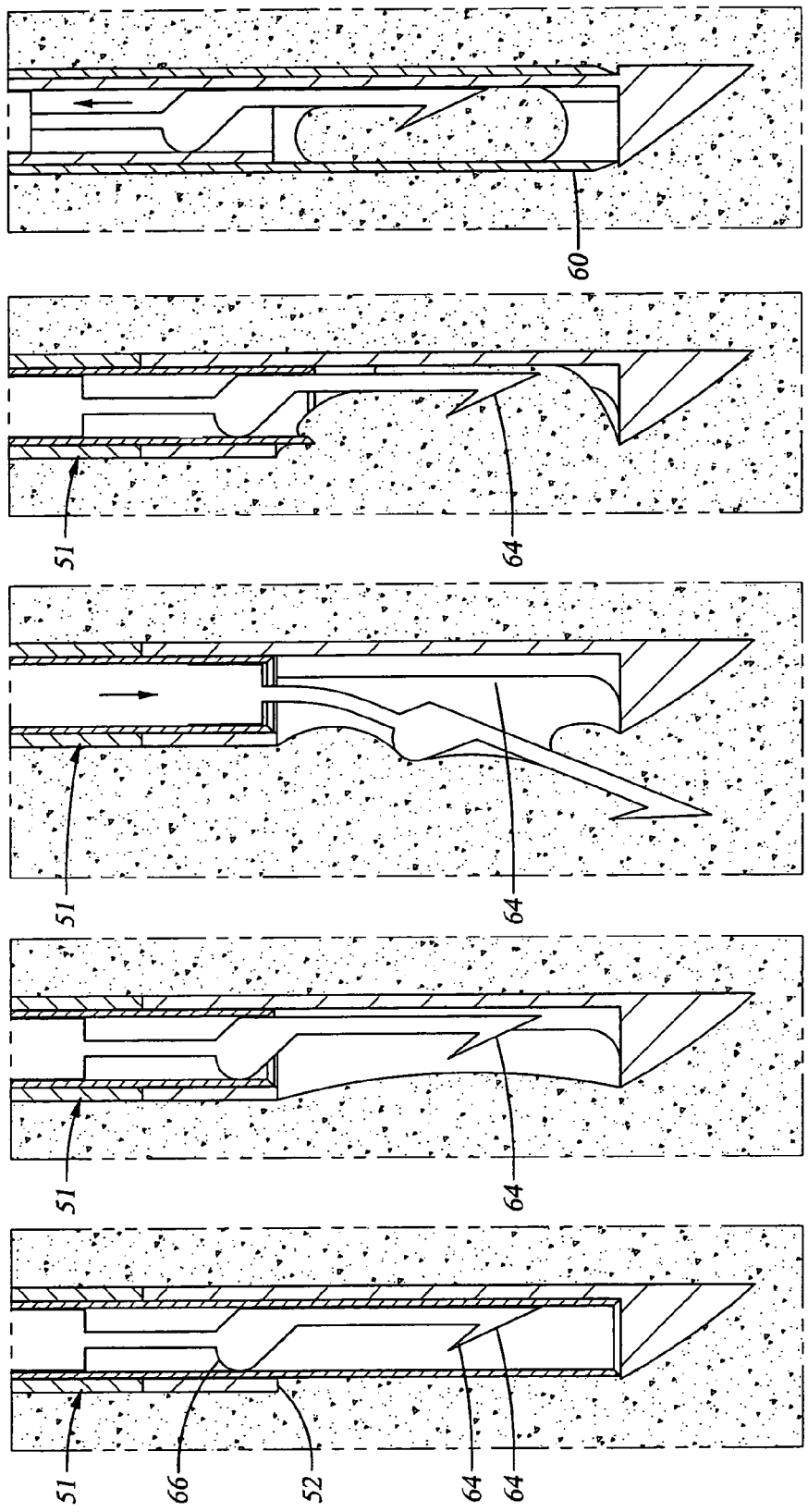

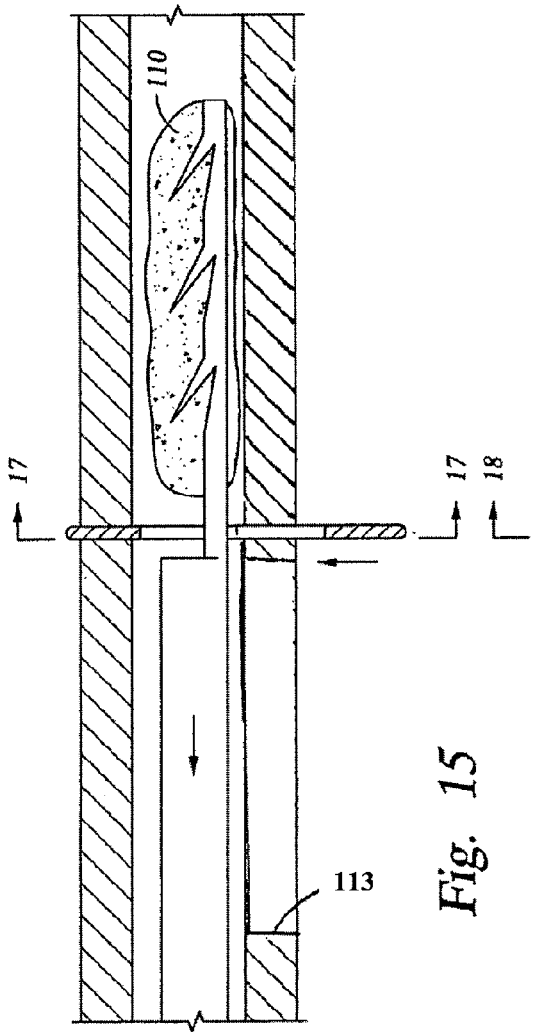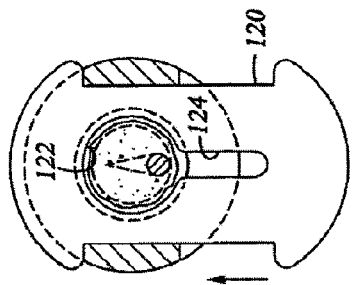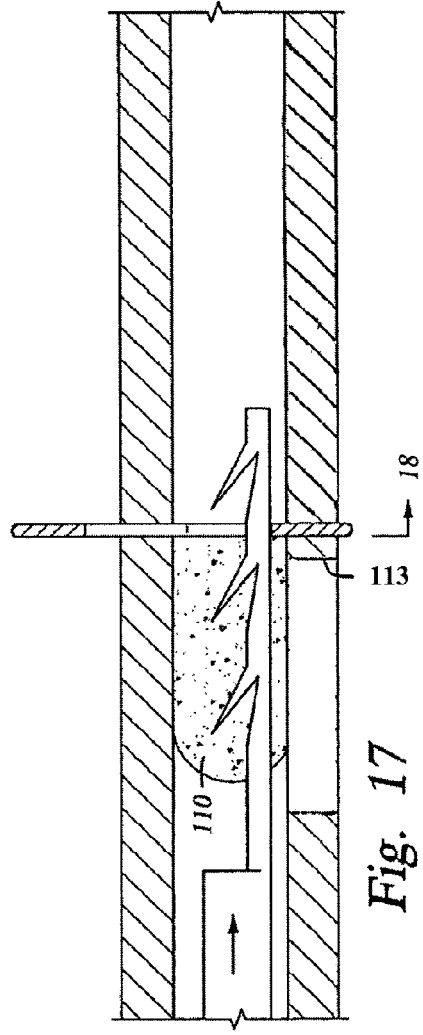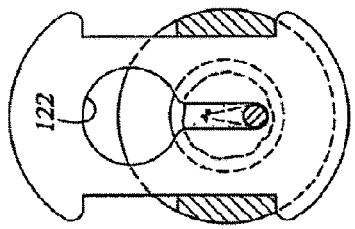

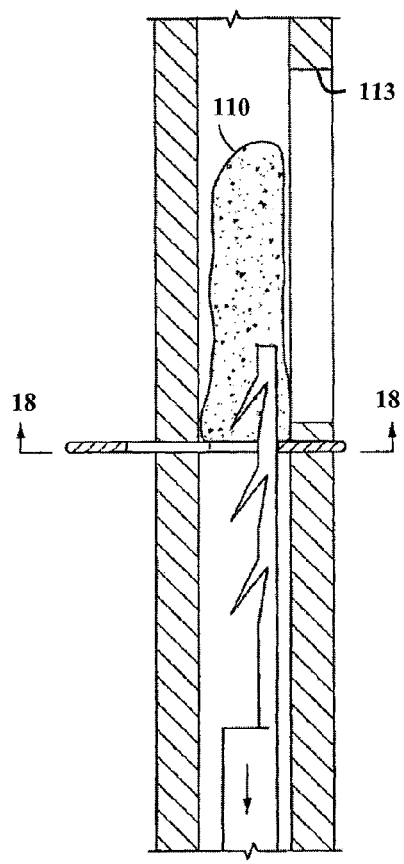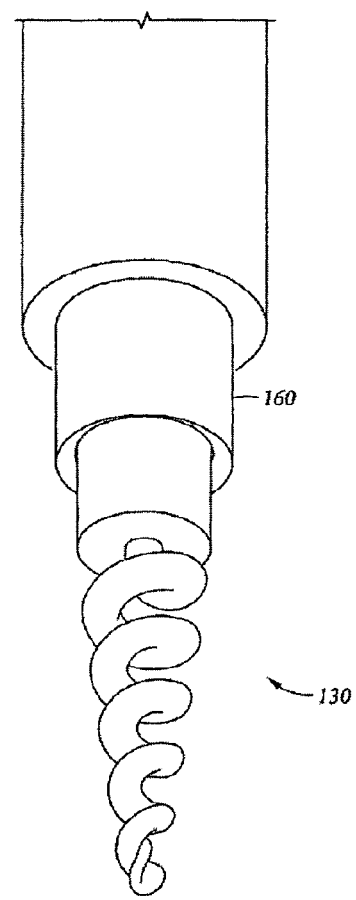
Fig. 30
Fig. 19

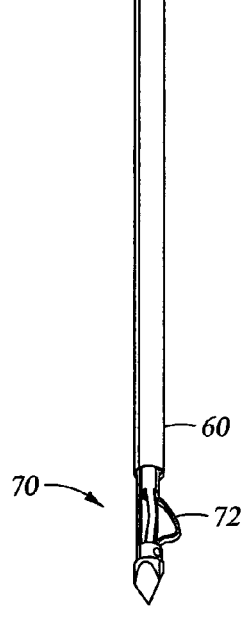
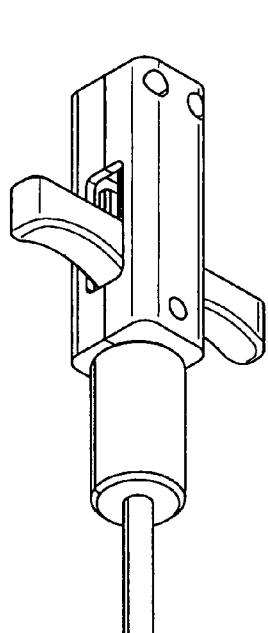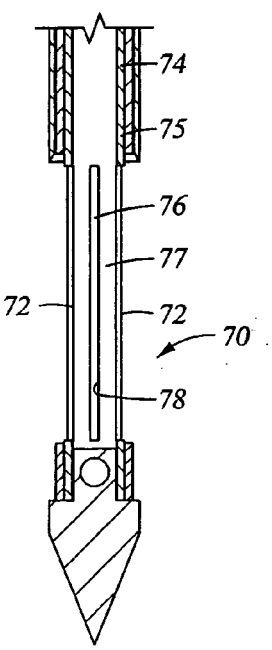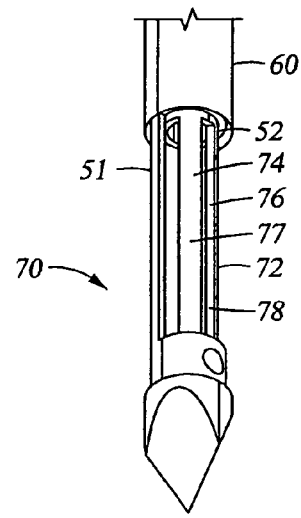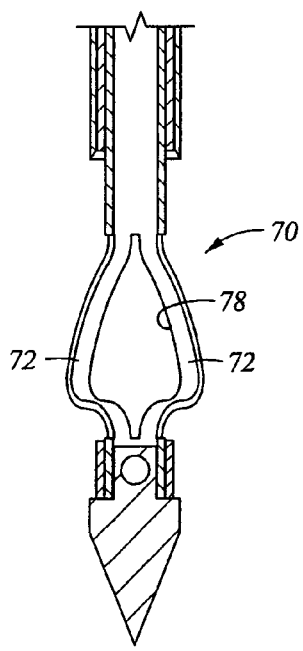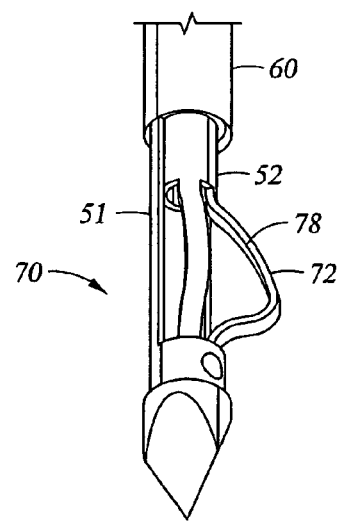
Fig. 20  Fig. 21  Fig. 22  Fig. 23  Fig. 24

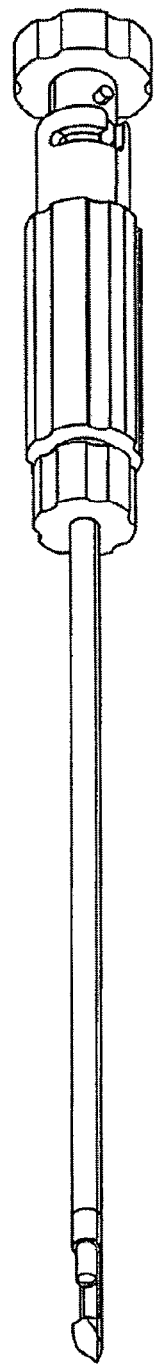 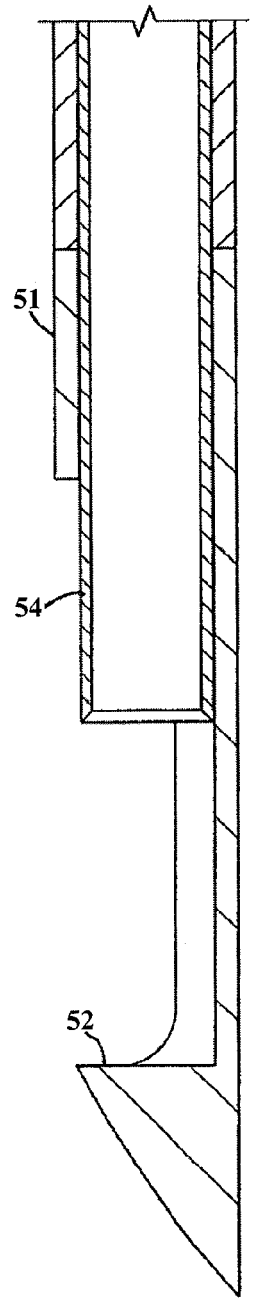 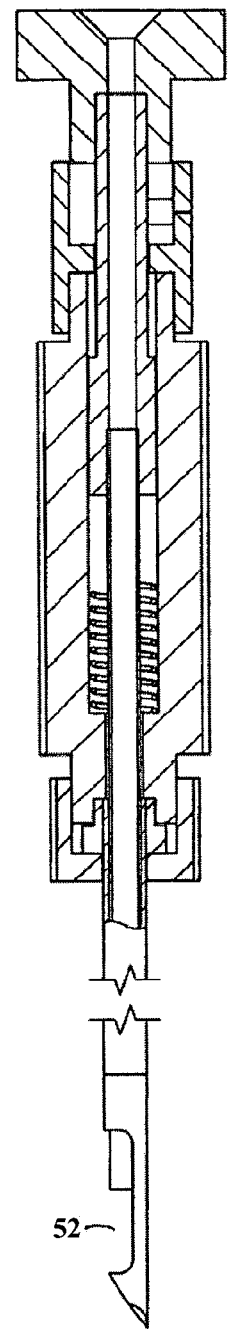
*Fig. 27*   *Fig. 28*   *Fig. 29*

SPINAL LIGAMENT MODIFICATION

CROSS-REFERENCE TO RELATED APPLICATIONS

This application claims benefit of U.S. application Ser. No. 60/592,099 filed Jul. 29, 2004, entitled "Device for Percutaneous Treatment of Spinal Stenosis," which is incorporated herein by reference in its entirety.

TECHNICAL FIELD OF THE INVENTION

The present invention relates to a minimally invasive method, device and system for treating spinal disorders using imaging guidance. This invention also relates to devices used to reduce stenosis and increase the cross-sectional area of the spinal canal and to devices used to treat excess fat within the spinal canal or epidural lipomatosis. This invention also relates to methods, devices, therapies and medications used to treat disorders that involve the epidural space.

BACKGROUND OF THE INVENTION

The spine comprises a stack of vertebrae with an intervertebral disc between adjacent vertebrae. As shown in FIG. 1, each vertebra 10 includes a vertebral body 12 that supports a bony ring 14. The bony ring 14 consists of laminae 16, spinous process 18, transverse processes 20, superior articular processes 22, and pedicles 24. Together with vertebral body 12, these vertebral components define the spinal canal. The laminae 16 are joined in the midline by the spinous process 18. In the cervical and thoracic region the dural sac 32 contains the spinal cord, which comprises nerves 34 surrounded by cerebrospinal fluid. The fluid-filled sac is therefore compressible. The ligamentum flavum 26 is an elastic yellow ligament connecting the laminae of adjacent vertebrae.

In degenerative conditions of the spine, narrowing of the spinal canal (stenosis) can occur. Lumbar spinal stenosis is often defined as a dural sac cross-sectional area less than 100 mm$_2$ or an anteroposterior (AP) dimension of the canal of less than 10-12 mm for an average male.

The source of most cases of lumbar spinal stenosis is thickening of the ligamentum flavum. Spinal stenosis may also be caused by subluxation, facet joint hypertrophy, osteophyte formation, underdevelopment of spinal canal, spondylosis deformans, degenerative intervertebral discs, degenerative spondylolisthesis, degenerative arthritis, ossification of the vertebral accessory ligaments and the like. A less common cause of spinal stenosis, which usually affects patients with morbid obesity or patients on oral corticosteroids, is excess fat in the epidural space. The excessive epidural fat compresses the dural sac, nerve roots and blood vessels contained therein and resulting in back and leg pain and weakness and numbness of the legs. Spinal stenosis may also affect the cervical and, less commonly, the thoracic spine.

Patients suffering from spinal stenosis are typically first treated with exercise therapy, analgesics and anti-inflammatory medications. These conservative treatment options frequently fail. If symptoms are severe, surgery is required to decompress the canal and nerve roots.

To correct stenosis in the lumbar region, an incision is made in the back and the muscles and supporting structures are stripped away from the spine, exposing the posterior aspect of the vertebral column. The thickened ligamentum flavum is then exposed by removal of the bony arch (lamina) covering the back of the spinal canal (laminectomy). The thickened ligament can then be excised with sharp dissection with a scalpel or punching instruments such as a Kerison punch that is used to remove small chips of tissue. The procedure is performed under general anesthesia. Patients are usually admitted to the hospital for approximately five to seven days depending on the age and overall condition of the patient. Patients usually require between six weeks and three months to recover from the procedure. Many patients need extended therapy at a rehabilitation facility to regain enough mobility to live independently.

Much of the pain and disability after an open laminectomy is due to the tearing and cutting of the back muscles, blood vessels and supporting ligaments and nerves that occurs during the exposure of the spinal column. Also, because these spine stabilizing back muscles and ligaments are stripped and cut off, the spine these patients frequently develop spinal instability post-operatively.

Minimally invasive techniques result in less post-operative pain and faster recovery compared to traditional open surgery. Percutaneous interventional spinal procedures can be performed with local anesthesia, thereby sparing the patient the risks and recovery time required with general anesthesia. Another advantage is that there is less damage to the paraspinal muscles and ligaments with minimally invasive techniques reducing pain and preserving these important stabilizing structures.

Various techniques for minimally invasive treatment of the spine are known. Microdiscectomy is performed by making a small incision in the skin and deep tissues to create a portal to the spine. A microscope is then used to aid in the dissection of the adjacent structures prior to discectomy. The recovery for this procedure is much shorter than traditional open discectomies. Percutaneous discectomy devices with fluoroscopic guidance have been used successfully to treat disorders of the disc but not to treat spinal stenosis or the ligamentum flavum directly. Arthroscopy or direct visualization of the spinal structures using a catheter or optical system have also been proposed to treat disorders of the spine including spinal stenosis however these devices still use miniaturized standard surgical instruments and direct visualization of the spine similar to open surgical procedures. These devices and techniques are limited by the small size of the canal and these operations are difficult to perform and master. Also these procedures are painful and often require general anesthesia. The arthroscopy procedures are time consuming and the fiber optic systems are expensive to purchase and maintain.

In addition, because the nerves of the spine pass through the core of the spine directly in front of the ligamentum flavum, any surgery, regardless of whether is open or percutaneous includes a risk of damage to those nerves.

Hence, it remains desirable to provide a simple method and device for treating spinal stenosis and other spinal disorders without requiring open surgery. It is further desired to provide a system whereby the risk of damage to the thecal sac containing the spinal nerves can be reduced.

SUMMARY OF THE INVENTION

The present invention provides a method, device and system for treating spinal stenosis or other spinal disorders using image guidance in combination with percutaneous techniques. The present system is referred to as a minimally invasive ligament decompression (MILD) device. In some embodiments, the present invention provides a means for compressing the thecal sac within the epidural space so as to provide a safety zone in which further surgical procedures may be performed without risk of damaging nearby tissues or the thecal sac itself.

In further embodiments, the present method comprises the steps of a) percutaneously accessing the epidural space in a region of interest with image guidance; b) at least partially compressing the thecal sac in the region of interest by injecting a fluid into the epidural space to form a safety zone; c) percutaneously accessing a working zone in at least one of the ligamentum flavum and overlying dorsal tissues with image guidance, where the safety zone lies between the working zone and thecal sac; d) inserting a tissue removal tool into the working zone; e) using the tool remove tissue so as to reduce the stenosis; and f) utilizing at least one imaging system to identify tissues for removal. By way of example, radiologic imaging may be used to safely guide the tool(s) to target tissues and visualize the position of the tool during at least part of the process.

In preferred embodiments, the device provides an anchored pathway to the working zone so that excised tissue can be shuttled out of the area for successive extractions without time consuming repositioning of the tool(s). In other embodiments, the tool can be repositioned as often as is necessary to achieve the desired modifications. In still other embodiments, the present invention includes percutaneous methods for placing a retractable anchor in the ligamentum flavum and attaching it to the fascia or bone so as to retract the ligamentum flavum, thus expanding the spinal canal. In still other embodiments, the invention includes a percutaneous mechanical suture system and method for placing a stitch in the ligament and then anchoring the stitch so as to retract the ligamentum flavum. The laminotomy site can serve as a site for a bone anchor and/or flange for a suture to anchor the ligament.

Particular embodiments of the invention include a method for treating stenosis in a spine, the spine including a thecal sac and a canal and an epidural space therebetween, wherein the stenosis determines a region of interest in the spine. The method may comprise the steps of a) percutaneously accessing the epidural space in the region of interest, b) compressing the thecal sac in the region of interest by injecting a fluid to form a safety zone and establish a working zone, with the safety zone lying between the working zone and the thecal sac, c) inserting a tissue removal tool into tissue in the working zone, d) using the tool to percutaneously reduce the stenosis. It is preferred to use at least one imaging system to visualize the position of the tool during at least a part of step d).

Step d) may include 1) engaging adjacent tissue in the working zone, 2) excising the engaged tissue, 3) removing the resulting tissue section from the working zone, and 4) repeating steps 1) through 3) until a desired amount of tissue has been removed. The removed tissue may comprise a portion of the ligamentum flavum, fat, and/or bone. Alternatively, the step d) may include i) providing an anchor having first and second tissue-engaging ends, ii) engaging the ligamentum flavum with the first tissue-engaging end, iii) using the engaged first end to pull at least a portion of the ligamentum flavum into a desired position, and iv) using the second tissue-engaging end to anchor the anchor such that the ligamentum flavum is retained in a desired position. The anchor may be anchored to paraspinous tissue or to other bone.

The invention also relates to an injectable fluid, which may include a contrast agent and may have a temperature-dependent viscosity such that it is more viscous at 37° C. than at 30° C.

The tool of steps c) and d) may include an outer cannulated scalpel or needle, a tissue-engaging means, and a cutting or resecting element and may further include means for removing tissue from the tissue-engaging means. The tissue-engaging means may comprise a resilient hook.

Some embodiments of the invention may take the form of a kit for performing a procedure on a spine, in which the kit includes an insertion member for accessing the epidural space, and an expandable device adapted to be inserted into the epidural space by the insertion member and expanded so as to compress a portion of the thecal sac and provide a safety zone within the epidural space. The expandable device may comprise a volume of a contrast medium, such as a radio-opaque non-ionic myelographic contrast medium, and/or may comprise a volume of a medium that is injectable at ambient temperatures and more viscous at body temperature. The contrast medium may include a bioactive agent and/or a steroid.

The kit may further include a surgical device, which in turn may comprise a hollow cannulated scalpel or outer needle having a side aperture proximal its distal end, and an elongate body housed within the outer needle and comprising two radially extendable arms constructed such that radially extending the arms causes them to extend outward through the side aperture and retracting said arms causes them to close. In other embodiments, the kit may comprise means for engaging the ligamentum flavum and means for resecting a section of the ligamentum flavum and the means for resecting may in turn comprise a trocar, a barbed member coaxially received within the trocar, and a blade. In other embodiments, the surgical device may comprise means for engaging a first anatomical structure and means for affixing the first anatomical structure to a second anatomical structure. Alternatively, the surgical device may comprise means for engaging the ligamentum flavum and soft tissues in the Para spinal region of the patient so as to anchor the ligamentum flavum, and/or means for engaging and retracting the ligamentum flavum and means for anchoring the retracted ligamentum flavum.

In still other embodiments, a percutaneous tool for treating a stenosed spine by removing tissue therefrom, comprises an cannulated scalpel, a first tissue-engaging means housed within the cannulated scalpel, and a cutting element configured to resect a sample of tissue that is engaged by the first tissue-engaging means. The cannulated scalpel may include a side aperture through which the first tissue-engaging means engages the tissue and the tool may further include a second tissue-engaging device that is adapted to remove the resected tissue sample from the first tissue-engaging device. The second tissue-engaging device may comprise a keyhole slot.

In still other embodiments, a device for removing tissue from a stenosed spine may comprise a hollow outer needle having a side aperture proximal its distal end, an elongate body housed within the outer needle and comprising two radially extendable arms constructed such that radially extending the arms causes them to extend outward through said side aperture and retracting the arms causes them to close. Each arm may include an opposing edge and at least one opposing edge may include teeth or ridges or the opposing edges may comprise cutting blades.

In certain embodiments, the present percutaneous tissue excision system may include an inner needle having one or more barbs extending around 120 degrees of its circumference. The barb(s) may be directed toward the proximal end of the needle. The tool may further include an occluding member that closes a side aperture in the cannula may include a distal cutting edge adapted to cut tissue. The tool may further comprise an outer cutting member. The tissue-engaging components of the device preferably comprise a resilient metal that can withstand repeated elastic deflections.

In yet further other embodiments, a method for preventing leakage of cerebrospinal fluid from an opening in a thecal sac in a spine may comprise accessing the epidural space in the vicinity of the opening and inserting a volume of fluid into the epidural space, where the fluid thickens as it attains body temperature such that the fluid blocks the opening in the thecal sac.

In further embodiments, a bone cutting device can be used to access the ligamentum flavum and epidural space, to perform a laminotomy or to allow placement of a cannula. Using a cannula fixed within (extending through) the lamina, a cutting device can be inserted into and removed from the ligamentum flavum and/or epidural space. Real-time use of fluoroscopy or other imaging means during the subsequent MILD procedure can be minimized with the appropriate placement of tools following use of the bone cutting device. The laminotomy creates a portal and gives a steady purchase for instruments and instrument exchange. In addition, either the laminotomy site or the neighboring tissue, including bone and/or other tissue, can be used as an anchoring site for sutures or other tissue-engaging means.

BRIEF DESCRIPTION OF THE DRAWINGS

For a more complete understanding of the invention, reference is made to the accompanying drawings, wherein:

FIGS. 5-9 are a series of illustrations showing tissue excision by a tissue-excision tool constructed in accordance with a first embodiment of the invention;

FIGS. 10-14 are a series of illustrations showing tissue excision by a tissue-excision tool constructed in accordance with a second embodiment of the invention;

FIGS. 15 and 17 are sequential illustrations showing removal of tissue from a tissue-excision tool by a tissue-removal device constructed in accordance with an embodiment of the invention;

FIGS. 16 and 18 are end views of the tissue-removal device of FIGS. 15 and 17, respectively;

FIG. 19 shows an alternative embodiment of a grasping needle with a corkscrew shape;

FIG. 20 is a perspective view of a tissue-excision tool constructed in accordance with a third embodiment of the invention;

FIGS. 21 and 22 are enlarged cross-sectional and perspective views, respectively, of the grasping device of FIG. 20 in its retracted position;

FIGS. 23 and 24 are enlarged cross-sectional and perspective views, respectively, of the grasping device of FIG. 20 in its extended position;

FIG. 27 is a perspective view of an entire tool constructed in accordance with preferred embodiments;

FIG. 28 is an enlarged cross-sectional view of the distal tip of the tool of FIG. 27 with the aperture partially opened;

FIG. 29 is a cross-sectional view of the handle end of the tool of FIG. 27;

FIG. 30 is cross-section of a tissue-removal device constructed in accordance with an alternative embodiment of the invention.

DETAILED DESCRIPTION OF THE PREFERRED EMBODIMENTS

The epidural space is the space between the ligamentum flavum and the thecal sac. This space is filled with blood vessels and fat. The nerves contained within the thecal sac are normally surrounded by cerebrospinal fluid (CSF). When the ligamentum flavum hypertrophies, the blood vessels that supply the nerves of the cauda equina are compressed. This results in ischemic pain termed spinal claudication. The nerve roots may also be compressed resulting in back and/or leg pain.

Referring again to FIG. 1, the posterior border of the normal epidural space 30 is formed by the normally thin ligamentum flavum 26 and posterior epidural fat (not shown). Ligamentum flavum 26 extends from the lamina above the interspinous space to the lamina below the interspinous space. The dural sleeve (thecal sac) 32 contains nerve roots 34 surrounded by cerebrospinal fluid. The nerve roots 34 normally comprise only a small proportion of the thecal sac volume.

Figures 1, 2:
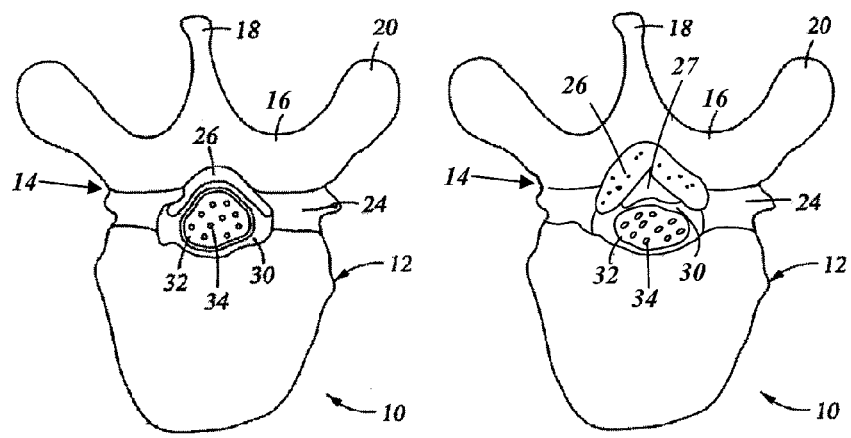
FIG. 1 is an illustration of a vertebra showing the spinal canal with the thecal sac and a normal (un-stenosed) ligamentum flavum therein.
FIG. 2 is an illustration of a vertebra showing the spinal canal with the thecal sac and a thickened ligamentum flavum therein.

In FIG. 2, spinal stenosis is present. Ligamentum flavum 26 is markedly thickened, compressing the posterior margin of dural sleeve 32. As shown in FIG. 2, the posterior margin of the dural sleeve 32 is apposed to the ligamentum flavum and the epidural space is only a potential space. Because more than 90% of the volume of the thecal sac in the lumbar region is filled by CSF, the thecal sac is highly compressible. Thus, even though stenosis may be causing compression of the thecal sac (and associated pain or discomfort), in most instances it will be possible to temporarily compress the thecal sac further. Thus, according to preferred embodiments of the invention, thecal sac 32 is compressed in a region of interest by applying pressure to the outside of the sac so that at least a portion of the CSF is forced out of the region of interest.

Creation of Safety Zone

Figures 3, 4:
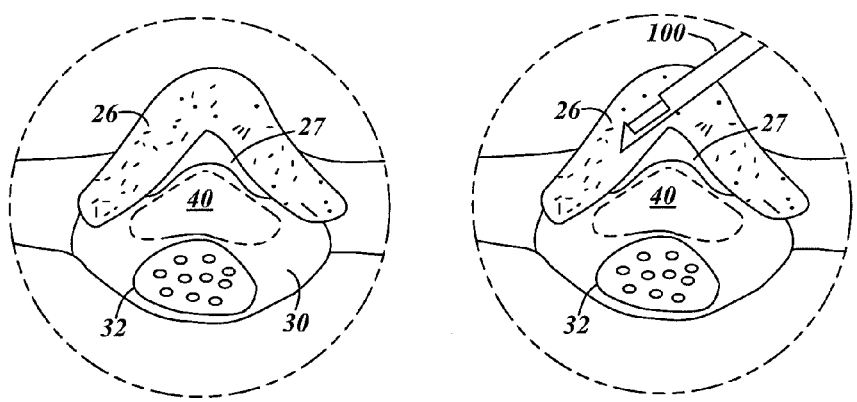
FIG. 3 is an enlarged cross-section of the spine of FIG. 2, showing a safety zone created by compression of the thecal sac.
FIG. 4 is the enlarged cross-section of FIG. 3, showing a tissue removal tool positioned in the ligamentum flavum.
Figure 25:
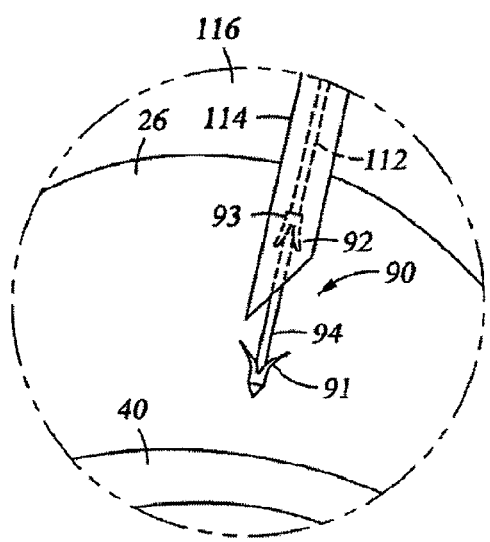
FIG. 25 is a schematic illustration of one embodiment of a double-ended ligament anchor being deployed in a ligamentum flavum.
Figure 26:
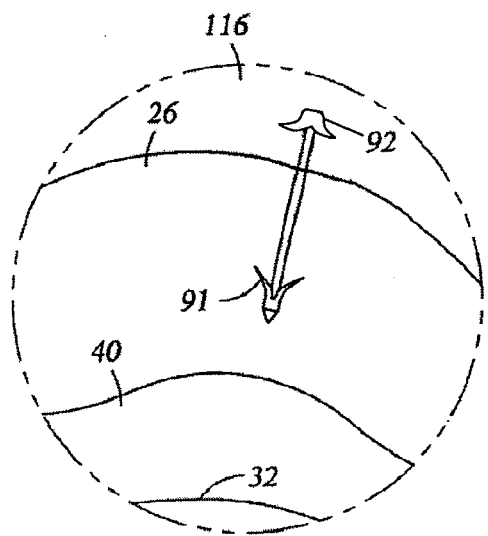
FIG. 26 shows the device of FIG. 25 after full deployment.

According to certain embodiments, thecal sac 32 is compressed by injecting a standard radio-opaque non-ionic myelographic contrast medium or other imagable or non-imagable medium into the epidural space in the region of interest. This is preferably accomplished with a percutaneous injection. The result is illustrated in FIG. 3. The presence of the fluid gently compresses and displaces the dural sleeve 32 in the region of interest, creating a safety zone 40 between thecal sac 32 and ligamentum flavum 26. Sufficient injectable fluid is preferably injected to displace the CSF out of the region of interest and compress the thecal sac to at least a desired degree. The injected medium is preferably substantially contained within the confines of the epidural space extending to the margins of the nerve root sleeves. The epidural space is substantially watertight and the fatty tissues and vascularization in the epidural space, combined with the viscous properties of the preferred fluids, serve to substantially maintain the injected medium in the desired region of interest. This novel method for protecting the neural column may be referred to hereinafter as "contrast-guided dural protection."

Once a safety zone 40 has been created, a tool 100, such as the tissue excision devices and tissue retraction devices described below, can be inserted into the ligamentum flavum 26, as illustrated in FIG. 4. While it is preferred that the tip of the tool remain within the ligament as shown, the presence of safety zone 40 ensures that the thecal sac will not be damaged even if the tool breaks through the anterior surface of ligament 26. For insertion of the tool, a fluoroscopic window of access (FWA) is defined by the inferior margin of the lamina (contra lateral to the point of instrument entry in the soft tissues) and the dorsal margin of the contrast material that defines the epidural space. This FWA is roughly orthogonal to the long axis of the cutting instrument, which parallels the inferior surface of the lamina as in FIG. 4. The fluoroscopic plane of projection is preferably but not necessarily oriented 20-45 degrees from normal (AP projection).

Because the present techniques are preferably performed percutaneously, certain aspects of the present invention can be facilitated by imaging. In this context, the spine can be imaged using any suitable technology, including but not limited to 2D, 3D fluoroscopy, CT, MRI, ultrasound or with direct visualization with fiber optic or microsurgical techniques. Stereotactic or computerized image fusion techniques are also suitable. Fluoroscopy is currently particularly well-suited to the techniques disclosed herein. Fluoroscopic equipment is safe and easy to use, readily available in most medical facilities, relatively inexpensive. In a typical procedure, using direct biplane fluoroscopic guidance and local anesthesia, the epidural space is accessed adjacent to the surgical site as described above.

If the injected medium is radio-opaque, as are for example myelographic contrast media, the margins of the expanded epidural space will be readily visible using fluoroscopy or CT imaging. Thus, the safety zone created by the present contrast-guided dural compression techniques can reduce the risk of damage to the spinal cord during procedures to remove or displace portions of the ligamentum flavum and/or laminae in order to treat spinal stenosis.

Injectable Medium

If desired, the injected medium can be provided as a re-absorbable water-soluble gel, so as to better localize the safety zone at the site of surgery and reduce leakage of this protective layer from the spinal canal. An injectable gel is a significant improvement on prior epidural injection techniques. The gel is preferably substantially more viscid than conventional contrast media and the relatively viscid and/or viscous gel preferably tends to remain localized at the desired site of treatment as it does not spread as much as standard liquid contrast media that are used in epidurography. The injected gel is preferably sufficiently viscous that it remains substantially within the local epidural space. This results in more uniform compression on the thecal sac and less leakage of contrast out of the canal. In addition, preferred embodiments of the gel are re-absorbed more slowly than conventional contrast media, allowing for better visualization during the course of the surgical procedure.

In some embodiments, a contrast agent can be included in the gel itself, so that the entire gel mass is imagable. In other embodiments, an amount of contrast can be injected first, followed by the desired amount of gel, or an amount of gel can be injected first, followed by the desired amount of contrast. In this case, the contrast agent is captured on the surface of the expanding gel mass, so that the periphery of the mass is imagable.

Any standard hydrophilic-lipophilic block copolymer (Pluronic) gel such as are known in the art would be suitable and other gels may be used as the injectable medium. The gel preferably has an inert base. In certain embodiments, the gel material is liquid at ambient temperatures and can be injected through a small bore (such as a 27 gauge needle). The gel then preferably becomes viscous when warmed to body temperature after being injected. The viscosity of the gel can be adjusted through the specifics of the preparation. The gel or other fluid is preferably sufficiently viscid or viscous at body temperature to compress and protect the thecal sac in the manner described above and to remain sufficiently present in the region of interest for at least about 30 minutes. Thus, in some embodiments, the injected gel attains a viscosity that is two, three, six or even ten times that of the fluids that are typically used for epidurograms.

In certain embodiments, the injected medium undergoes a reversible change in viscosity when warmed to body temperature so that it can be injected as a low-viscosity fluid, thicken upon injection into the patient, and be returned to its low-viscosity state by cooling. In these embodiments, the injected medium is injected as desired and thickens upon warming, but can be removed by contacting it with a heat removal device, such as an aspirator that has been provided with a cooled tip. As a result of localized cooling, the gel reverts to its initial non viscous liquid state and can be easily suctioned up the cooled needle or catheter.

An example of a suitable contrast medium having the desired properties is Omnipaque® 240 available from Nycomed, New York, which is a commercially available non-ionic iodinated myelographic contrast medium. Other suitable injectable media will be known to those skilled in the art. Because of the proximity to the spinal nerves, it is preferred not to use ionic media in the injectable medium. The preferred compositions are reabsorbed relatively rapidly after the procedure. Thus any residual gel compression on the thecal sac after the MILD procedure resolves relatively quickly. For example, in preferred embodiments, the gel would have sufficient viscosity to compress the thecal sac for thirty minutes, and sufficient degradability to be substantially reabsorbed within approximately two hours.

The injected contrast medium further may further include one or more bioactive agents. For example, medications such as those used in epidural steroid injection (e.g. Depo medrol, Celestone Soluspan) may be added to the epidural gel to speed healing and reduce inflammation, scarring and adhesions. The gel preferably releases the steroid medication slowly and prolongs the anti-inflammatory effect, which can be extremely advantageous. Local anesthetic agents may also be added to the gel. This prolongs the duration of action of local anesthetic agents in the epidural space to prolong pain relief during epidural anesthesia. In this embodiment the gel may be formulated to slow the reabsorption of the gel.

The present gels may also be used for epidural steroid injection and perineural blocks for management of acute and chronic spinal pain. Thrombin or other haemostatic agents can be added if desired, so as to reduce the risk of bleeding.

In some embodiments, the gel may also be used as a substitute for a blood patch if a CSF leak occurs. The gel may also be used as an alternative method to treat lumbar puncture complications such as post-lumbar puncture CSF leak or other causes of intracranial hypotension. Similarly, the gel may be used to patch postoperative CSF leaks or dural tears. If the dural sac were inadvertently torn or cut, then gel could immediately serve to seal the site and prevent leakage of the cerebral spinal fluid.

Percutaneous Tissue Excision

After safety zone 40 has been created, the margins of the epidural space are clearly demarcated by the injected medium and can be visualized radiographically if an imagable medium has been used. As mentioned above, percutaneous procedures can now safely be performed on the ligamentum flavum and/or surrounding tissues without injuring the dural sac or nerves and the spinal canal can be decompressed using any of several techniques. Suitable decompression techniques include removal of tissue from the ligamentum flavum, laminectomy, laminotomy, and ligament retraction and anchoring.

In some embodiments, all or a portion of the ligamentum flavum and/or lamina are excised using a percutaneous tissue excision device or probe 100, which may hereinafter be referred to as the MILD device. As shown schematically in FIG. 4, a device 100 may be placed parallel to the posterior and lateral margin of the safety zone 40 with its tip in the ligamentum flavum 26.

Preferred embodiments of the present tissue excision devices and techniques can take several forms. In the discussion below, the distal ends of the tools are described in detail. The construction of the proximal ends of the tools, and the means by which the various components disclosed herein are assembled and actuated, will be known and understood by those skilled in the art.

By way of example, in the embodiment shown in FIG. 4 and as illustrated in FIG. 5, device 100 may be a coaxial excision system 50 with a sharpened or blunt tip that is placed obliquely into the thickened ligamentum flavum 26 posterior to safety zone 40 under fluoroscopic guidance. The needle is preferably placed parallel to the posterior margin of the canal. Excision system 50 is preferably manufactured from stainless steel, titanium or other suitable durable biocompatible material. As shown in FIGS. 5-10, an outer needle or cannula 51 has an opening or aperture 52 on one side that is closed during insertion by an inner occluding member 54. Aperture 52 is readily visible under imaging guidance. Once needle 51 is positioned in the ligamentum flavum or other tissue removal site, inner occluding member 54 is removed or retracted so that it no longer closes aperture 52 (FIG. 6). Aperture 52 is preferably oriented away from the epidural space so as to further protect the underlying structures from injury during the surgical procedure. If it was not already present in the tool, a tissue-engaging means 56 is inserted through outer needle 51 to aperture 52 so that it contacts adjacent tissue, e.g. the ligamentum flavum, via aperture 52.

Tissue-engaging means 56 may be a needle, hook, blade, tooth or the like, and preferably has at least one flexible barb or hook 58 attached to its shaft. The barb 58 or barbs may extend around approximately 120 degrees of the circumference of the shaft. Barbs 58 are preferably directed towards the proximal end of the tool. When needle 56 is retracted slightly, barbs 58 allow it to engage a segment of tissue. Depending on the configuration of barbs 58, the tissue sample engaged by needle 56 may be generally cylindrical or approximately hemispherical. Once needle 56 has engaged the desired tissue, inner occluding means 54, which is preferably provided with a sharpened distal edge, is advanced so that it cuts the engaged tissue section or sample loose from the surrounding tissue. Hence occluding means 54 also functions as a cutting means in this embodiment. In alternative embodiments, such as FIGS. 10-14 discussed below, a cylindrical outer cutting element 60 may extended over outer needle 51 and used in place of occluding member 54 to excise the tissue sample.

Referring still to FIGS. 5-9, once the tissue sample has been cut, tissue-engaging needle 56 can be pulled back through outer needle 51 so that the segment of tissue can be retrieved and removed from the barbs (FIG. 8). The process or engaging and resecting tissue may be repeated (FIG. 9) until the canal is adequately decompressed.

Referring briefly to FIGS. 10-14, in other embodiments, a tissue-engaging hook 64 can be used in place of needle 56 and an outer cutting member 60 can be used in place of inner occluding member 54. Hook 64 may comprise a length of wire that has been bent through at least about 270°, more preferably through 315°, and still more preferably through about 405°. Alternatively or in addition, hook 64 may comprise Nitinol™, or any other resilient metal that can withstand repeated elastic deflections. In the embodiment illustrated, hook 64 includes at least one barb 58 at its distal end. In some embodiments, hook 64 is pre-configured in a curvilinear shape and is retained within tool 100 by outer cutting member 60. When cutting member 60 is retracted, the curved shape of hook 64 urges its outer end to extend outward through aperture 52. If desired, hook 64 can be advanced toward the distal end of tool 100, causing it to extend farther into the surrounding tissue. In some embodiments, hook 64 is provided with a camming surface 66. Camming surface 66 bears on the edge of opening 52 as hook 64 is advance or retracted and thereby facilitates retraction and retention of hook 64 as it is retracted into the tool. In these embodiments, hook 64 may not extend through aperture 52 until it has been advanced sufficiently for camming surface 66 to clear the edge of the opening. Hook 64 may alternatively be used in conjunction with an inner occluding member 54 in the manner described above. As above, hook 64 can be used to retrieve the engaged tissue from the distal end of the tool.

In still other embodiments, the tissue-engaging means may comprise a hook or tooth or the like that engages tissue via aperture 52 by being rotated about the tool axis. In such embodiments (not shown) and by way of example only, the tissue-engaging means could comprise a partial cylinder that is received in outer cannula 51 and has a serrated side edge. Such a device can be rotated via a connection with the tool handle or other proximal device. As the serrated edge traverses aperture 52 tissue protruding into the tool via the aperture is engaged by the edge, whereupon it can be resected and retrieved in the manner disclosed herein.

In preferred embodiments, the working tip of tool 100 remains within the ligamentum flavum and does not penetrate the safety zone 40. Nonetheless, safety zone 40 is provided so that even an inadvertent penetration of the tool into the epidural space will not result in damage to the thecal sac. Regardless of the means by which the tissue is engaged and cut, it is preferably retrieved from the distal end of the tool so that additional tissue segments can be excised without requiring that the working tip of the tool be repositioned. A tissue-removal device such as that described below is preferably used to remove the tissue from the retrieval device between each excision.

Tissue Removal

Each piece of tissue may be removed from barbs 58 by pushing tissue-engaging means 56 through an opening that is large enough to allow passage of the flexible barbs and supporting needle but smaller than the diameter of the excised tissue mass. This pushes the tissue up onto the shaft, where it can be removed with a slicing blade or the like or by sliding the tissue over the proximal end of the needle. Alternatively, needle 56 can be removed and re-inserted into the tool for external, manual tissue removal.

It is expected that in some embodiments, approximately 8-10 cores or segments of tissue will be excised and pushed up the shaft towards the hub during the course of the procedure. Alternatively, a small blade can be used to split the tissue segment and thereby ease removal of the segment from the device. If desired, a blade for this purpose can be placed on the shaft of needle 56 proximal to the barbs.

In an exemplary embodiment, shown in FIGS. 15-18, the tissue removal device may include a scraper 120 that includes a keyhole slot having a wide end 122 and a narrow end 124. To remove a tissue sample from needle 56 or hook 64, the tissue-engaging device with a mass of excised tissue 110 thereon can be retracted (pulled toward the proximal end of the tool) through wide end 122 of the slot and then re-inserted (pushed toward the distal end of the tool) through narrow end 124 of the slot. Narrow end 124 is large enough to allow passage of the barbed needle, but small enough to remove the tissue mass as the needle passes through. By shuttling the tissue-engaging device through scraper 120 in this manner, each excised segment of tissue 110 can be removed from the device, readying the device for another excision.

In an alternative embodiment (not shown) an alternative mechanism for removing the tissue segment from needle 56 includes an adjustable aperture in a disc. After the tissue-bearing needle is pulled back through the aperture, the aperture is partially closed. Needle 56 and flexible hooks 58 then can pass through the partially closed aperture but the larger cylinder of tissue cannot. Thus the tissue segment is pushed back onto the shaft. The tissue segment can either be pulled off the proximal end of the shaft or cut off of it. A small blade may be placed just proximal to the barbs to help cut the tissue segment off the shaft. The variable aperture can formed by any suitable construction, including a pair of metal plates with matching edges that each define one half of a central opening. The two pieces may be held apart by springs. The aperture may be closed by pushing the two edges together. In other embodiments, this process can be mechanically automated by using a disc or plate with an opening that is adjustable by a variety of known techniques, including a slit screw assembly or flexible gaskets.

Alternative Tissue Excision Devices

Other cutting and/or grasping devices can be used in place of the system described above. For example, embodiments of the grasping mechanism include but are not limited to: needles with flexible barbs, needles with rigid barbs, corkscrew-shaped needles, and/or retaining wires. The corkscrew-shaped needle shown in FIG. 19 works by screwing into the ligamentum flavum in the manner that a corkscrew is inserted in a cork. After the screw engages a segment of tissue, outer cutting element 60 slides over the needle, cutting a segment of tissue in a manner similar to that of the previous embodiment. In some embodiments, the cutting element can be rotated as it cuts.

In other embodiments, shown in FIGS. 20-22, cannulated scalpel 51 houses a grasping device 70 that includes at least one pair of arcuate, closable arms 72. Closable arms 72 may be constructed in any suitable manner. One technique for creating closable arms is to provide a slotted sleeve 74, as shown. Slotted member 74 preferably comprises an elongate body 75 with at least one slot 76 that extends through its thickness but does not extend to either end of the body. Slot 76 is preferably parallel to the longitudinal axis of the sleeve. On either side of slot 76, a strip 77 is defined, with strips 77 being joined at each end of sleeve 74. It is preferred that the width of each strip 77 be relatively small. In some embodiments, it may be desirable to construct slotted member 74 from a portion of a hollow tube or from a rectangular piece that has been curved around a longitudinal axis. The inner edge of each strip that lies along slot 76 forms an opposing edge 78. The width of the piece is the total of the width of strips 77 and slot 76.

Advancing one end of sleeve 74 toward the other end of sleeve 74 causes each strip 77 to buckle or bend. If strips 77 are prevented from buckling inward or if they are predisposed to bend in the desired direction, they will bend outward, thereby forming arcuate arms 72, which extend through aperture 52 of cannulated scalpel 51, as shown in FIG. 21. As they move away from the axis of body 75, arms 72 move apart in a direction normal to the axis of body 75. Likewise, moving the ends of sleeve 74 apart causes arms 72 to straighten and to move together and inward toward the axis of the device, as shown in FIG. 22. As the arms straighten, opposing edges 78 close and a segment of tissue can be capture between them. Tissue within the grasping device may then be resected or anchored via the other mechanisms described herein.

Closable arms 72 may include on their opposing edges 78 ridges, teeth, or other means to facilitate grasping of the tissue. In other embodiments, edges 78 may be sharpened, so as to excise a segment of tissue as they close. In these embodiments, closable arms 72 may also be used in conjunction with a hook, barbed needle, pincers or the like, which can in turn be used to retrieve the excised segment from the device.

Once arms 72 have closed on the tissue, if arms 72 have not cut the tissue themselves, the tissue can be excised using a blade such as cutting element 60 above. The excised tissue can be removed from the inside of needle 51 using a tissue-engaging hook 64 or other suitable means. The process of extending and closing arms 72, excising the tissue, and removing it from the device can be repeated until a desired amount of tissue has been removed.

If desired, this cycle can be repeated without repositioning the device in the tissue. Alternatively, the tool can be rotated or repositioned as desired between excisions. It is possible to rotate or reposition the tool during an excision, but it is expected that this will not generally be preferred. Furthermore, it is expected that the steps of tissue excision and removal can be accomplished without breaching the surface of the ligament, i.e. without any part of the device entering the safety zone created by the injected fluid. Nonetheless, should the tool leave the working zone, the safety zone will reduce the risk of injury to the thecal sac.

Ligament Retraction

In some embodiments, the spinal canal may also be enlarged by retracting the ligamentum flavum, either with or without concurrent resection. Retraction is preferably but not necessarily performed after dural compression has been used to provide a safety zone. In addition, the dural compression techniques described above have the effect of pressing the ligamentum flavum back out of the spinal canal and thereby making it easier to apply a restraining means thereto.

Thus, in preferred embodiments, after a safety zone is created by epidural injection of contrast medium or gel, a retraction device 90 as shown in FIG. 23 is used to retract and compress the thickened soft tissues around the posterior aspect of the spinal canal, thereby increasing the available space for the dural sac and nerves. In the embodiment shown, retraction device 90 is a double-headed anchor that includes at least one distal retractable tissue-engaging member 91 and at least one proximal tissue-engaging member 92, each of which are supported on a body 94. Retraction device 90 is preferably constructed from an implantable, non-biodegradable material, such as titanium or stainless steel, but may alternatively be polymeric or any other suitable material. In certain preferred embodiments, body 94 is somewhat flexible. In some instances, flexibility in body 94 may facilitate the desired engagement of barbs 91, 92. Barbs 91, 92 may comprise hooks, arms, teeth, clamps, or any other device capable of selectively engaging adjacent tissue. Barbs 91, 92 may have any configuration that allows them to engage the ligamentum flavum and/or surrounding tissue. Similarly, barbs 91, 92 may be covered, sheathed, pivotable, retractable, or otherwise able to be extended from a first position in which they do not engage adjacent tissue to a second position in which they can engage adjacent tissue.

FIG. 23 shows schematically the distal and proximal retractable arms 91, 92 of a preferred ligament anchor 90. The proximal end of the anchor preferably includes a threaded connector 96 or other releasable mechanism that attaches to a support rod 100. Ligament anchor 90 may be attached to a support shaft 112 and sheathed in a guide housing 114. The distal and proximal barbs 91, 92 are prevented by guide housing 114 from engaging surrounding tissue. Housing 102 is preferably a metal or durable plastic guide housing.

The distal end of the device is preferably positioned in the ligamentum flavum under fluoroscopic guidance. If desired, an accessway through the lamina may be provided using an anchored cannula or the like. The device is held in position by support shaft 112. Distal barbs 91 are unsheathed and optionally expanded by pulling back guide housing 102, as shown in FIG. 23. Distal barbs 91 are secured in the ligamentum flavum by pulling back on the support shaft 112. With barbs 91 engaging the tissue, the ligamentum flavum is retracted posteriorly by pulling back on support shaft 112. While maintaining traction on the now-retracted ligament, proximal barbs 92 are uncovered and expanded by retracting guide housing 114, as shown in FIG. 24. Barbs 92 are preferably positioned in the soft tissues 116 in the para-spinal region so that the device is firmly anchored behind the posterior elements of the spinal canal. Once the proximal end of the anchor is engaged, support shaft 112 may be detached from body 94 as shown in FIG. 24. In this manner, the posterior margin 95 of the ligamentum flavum can be held in a retracted position, thereby expanding the canal. The procedure can then be repeated on adjacent portions of the ligamentum flavum until it is sufficiently retracted.

In an alternative embodiment, the proximal end of ligament anchor 90 may be adapted to engage the lamina. This may be accomplished by having the arm posterior to the lamina or by using the laminotomy and suturing the device to the lamina there. A knotted or knotless system or a suture plate can be used.

A second embodiment of the present method uses a plurality of retraction devices 90. In this embodiment, the retraction device is inserted through one lamina in an oblique fashion, paralleling the opposite lamina. After the distal anchor is deployed, the retraction device is pulled back and across the ligamentum flavum, thereby decompressing the opposite lateral recess of the spinal canal. This is repeated on the opposite side. This same device can also be deployed with a direct approach to the lateral recess with a curved guide housing.

While retraction device 90 is describe above as a double-headed anchor, it will be understood that other devices can be used. For example sutures, barbed sutures, staples or the like can be used to fasten the ligament in a retracted position that reduces stenosis.

Using the percutaneous methods and devices described herein, significant reductions of stenosis can be achieved. For example, a dural sac cross-sectional area less than 100 $mm^2$ or an anteroposterior (AP) dimension of the canal of less than 10-12 mm in an average male is typically considered relative spinal stenosis. A dural sac cross-sectional area less than 85 $mm^2$ in an average male is considered severe spinal stenosis. The present devices and techniques are anticipated to cause an increase in canal area of 25 $mm^2$ per anchor or 50 $mm^2$ total. With resection and/or retraction of the ligamentum flavum, the cross-sectional area of the dural sac can be increased by 10 $mm^2$, and in some instances by as much as 20 $mm^2$ or even 30 $mm^2$. Likewise, the present invention can result in an increase of the anteroposterior dimension of the canal by 1 to 2 mm and in some instances by as much as 4 or 6 mm. The actual amount by which the cross-sectional area of the thecal sac and/or the anteroposterior dimension of the canal are increased will depend on the size and age of the patient and the degree of stenosis and can be adjusted by the degree of retraction of the ligament.

MILD

The minimally invasive ligament decompression (MILD) devices and techniques described herein allow spinal decompression to be performed percutaneously, avoiding the pain and risk associated with open surgery. Through the provision of a safety zone, the present devices and techniques offer reduced risk of spinal cord damage. In addition to improving nerve function, it is expected that decompression of the spinal canal in the manner described herein will result in improved blood flow to the neural elements by reducing the extrinsic pressure on the spinal vasculature. For these reasons, it is believed that spinal decompression performed according to the present invention will be preferable to decompression operations performed using currently known techniques.

Dural Shield

In some embodiments (not shown), a mechanical device such as a balloon or mechanical shield can also be used to create a protective guard or barrier between the borders of the epidural space and the adjacent structures. In one embodiment a durable expandable device is attached to the outside of the percutaneous laminectomy device, preferably on the side opposite the cutting aperture. The cutting device is inserted into the ligamentum flavum with the expandable device deflated. With the aperture directed away from the spinal canal, the expandable device is gently expanded via mechanical means or inflated with air or another sterile fluid, such as saline solution, via a lumen that may be within or adjacent to the body of the device. This pushes the adjacent vital structures clear from the cutting aperture of the device and simultaneously presses the cutting aperture into the ligament. As above, the grasping and cutting needles can then be deployed and operated as desired. The balloon does not interfere with tissue excision because it is located on the side opposite the cutting aperture. The cutting needle may be hemispherical (semi-tubular) in shape with either a straight cutting or a sawing/reciprocating blade or may be sized to be placed within the outer housing that separates the balloon from the cutting aperture.

In another embodiment, a self-expanding metal mesh is positioned percutaneously in the epidural space. First the epidural space is accessed in the usual fashion. Then a guide catheter is placed in the epidural space at the site of the intended surgical procedure. The mesh is preferably compressed within a guide catheter. When the outer cover of the guide catheter is retracted, the mesh expands in the epidural space, protecting and displacing the adjacent dural sheath. At the conclusion of the surgical procedure, the mesh is pulled back into the guide sheath and the assembly removed. The mesh is deformable and compresses as it is pulled back into the guide catheter, in a manner similar to a self-expanding mesh stent. There are many commercially available self-expanding stents approved and in use in other applications. However, using a self-expandable mesh as a device within the epidural space to protect and displace the thecal sac is novel.

While preferred embodiments of this invention have been shown and described, modifications thereof can be made by one skilled in the art without departing from the scope or teaching of this invention. For example, the means by which the safety zone is formed may be varied, the shape and configuration of the tissue excision devices may be varied, and the steps used in carrying out the technique may be modified. Accordingly, the invention is not limited to the embodiments described herein, but is only limited by the claims that follow, the scope of which shall include all equivalents of the subject matter of the claims. Likewise, the sequential recitation of steps in a claim, unless explicitly so stated, is not intended to require that the steps be performed in any particular order or that a particular step be completed before commencement of another step.

What is claimed is:

1. A method for treating stenosis in a spine, the spine including a thecal sac, a canal, an epidural space between the thecal sac and the canal, and a ligamentum flavum, the stenosis determining a region of interest in the spine, comprising the steps of:
   a) compressing the thecal sac in the region of interest by injecting a fluid into the epidural space to form a modified epidural space and a safety zone and establish a working zone, the safety zone lying generally within the modified epidural space, and the working zone lying generally outside the modified epidural space and generally posterior to the thecal sac, wherein the working zone is outside the safety zone;
   b) inserting a tool into tissue in the working zone without breaching an anterior surface of the ligamentum flavum;
   c) using the tool to percutaneously reduce the stenosis by excising a portion of tissue in the working zone; and
   d) utilizing imaging to visualize the position of the tool during at least a part of step c).

2. The method of claim 1 wherein the tool comprises:
   a cannula comprising a tissue-penetrating member having a distal end defining an aperture on one side thereof;
   an occluding member slidably received on or in said cannula and closing said aperture when said occluding member is adjacent said cannula distal end;
   means for engaging adjacent tissue via said aperture; and
   cutting means for resecting a section of said engaged tissue.

3. The method of claim 2 wherein the tool further includes means for retrieving said resected tissue from said distal tool end and a tissue-removal system for removing tissue from said retrieving means.

4. The method of claim 1 wherein step c) comprises
   c1) engaging a tissue sample in the working zone;
   c2) excising the tissue sample;
   c3) removing the tissue sample from the working zone; and
   c4) repeating steps c1) through c3) until a desired amount of tissue has been removed.

5. The method of claim 4 wherein the tissue sample comprises tissue selected from the group consisting of the ligamentum flavum, fat, and bone.

6. The method of claim 4 wherein step c) is carried out without repositioning the device in the tissue.

7. The method of claim 4 wherein step c) comprises
   ci) providing an anchor having first and second tissue-engaging ends;
   cii) engaging the ligamentum flavum with said first tissue-engaging end;
   ciii) using said engaged first end to pull at least a portion of the ligamentum flavum into a desired position; and
   civ) using said second tissue-engaging end to anchor said anchor such that said
   ligamentum flavum is retained in a desired position.

8. The method of claim 7 wherein step civ) comprises anchoring said anchor to paraspinous tissue.

9. The method of claim 7 wherein step civ) comprises anchoring said anchor to bone.

10. The method of claim 1 wherein the injected fluid includes a contrast medium.

11. The method of claim 10 wherein the injected fluid has a temperature-dependent viscosity and is more viscous at 37° C. than at 30° C.

12. The method of claim 1 wherein the tool includes an outer cannulated scalpel, a tissue engaging means received in said scalpel, and a cutting element.

13. The method of claim 12 wherein the tool further includes means for removing tissue from the tissue-engaging means.

14. The method of claim 12 wherein the tissue-engaging means comprises a resilient hook.

15. A method for treating stenosis in a spine, the spine including a thecal sac and an epidural space, the stenosis determining a region of interest in the spine, comprising the steps of:
   a) compressing the thecal sac in the region of interest by injecting a fluid into the epidural space to form a modified epidural space and a safety zone and establish a working zone, the safety zone lying generally within the modified epidural space, and the working zone lying generally outside the modified epidural space, wherein the working zone is outside the safety zone;
   b) inserting a tool into tissue in the working zone;
   c) using the tool to percutaneously reduce the stenosis by excising a portion of tissue in the working zone, while maintaining an anterior surface of a ligamentum flavum; and
   d) utilizing imaging to visualize the position of the tool during at least a part of step c).

16. The method of claim 15 wherein an anterior surface of a lamina is maintained during step c).

17. The method of claim 16 wherein the working zone lies generally posterior to the thecal sac.

18. A method for treating stenosis in a spine, the spine including a thecal sac and an epidural space, the stenosis determining a region of interest in the spine, comprising the steps of:
   a) compressing the thecal sac in the region of interest by injecting a fluid into the epidural space to form a modified epidural space and a safety zone and establish a working zone, the safety zone lying generally within the modified epidural space, and the working zone lying generally outside the modified epidural space, wherein the working zone is outside the safety zone;
   b) inserting a tool into tissue in the working zone;
   c) using the tool to percutaneously reduce the stenosis by excising a portion of tissue in the working zone; and
   d) utilizing fluoroscopic imaging to visualize the position of the tool during at least a part of step c).

19. The method of claim 18 further comprising utilizing fluoroscopic imaging to visualize the position of the tool throughout all steps of the method of claim 18.

20. The method of claim 18 further comprising utilizing a radio-opaque die outside of the tool.

* * * * *